United States Patent [19]

Dauben et al.

[11] Patent Number: 4,490,226

[45] Date of Patent: Dec. 25, 1984

[54] EFFICIENT PHOTOCHEMICAL FORMATION OF 1-α-HYDROXYPREVITAMIN D$_3$

[75] Inventors: William G. Dauben, Berkeley, Calif.; Phillip R. Jeffries, Cottesloe, Australia; Richard B. Phillips, East Windsor, N.J.

[73] Assignee: The Regents of The University of California, Calif.

[21] Appl. No.: 413,180

[22] Filed: Aug. 30, 1982

[51] Int. Cl.$^3$ ............................................. B01J 19/12
[52] U.S. Cl. .................................................. 204/159
[58] Field of Search ......................... 204/159, 158 ST

[56] References Cited

U.S. PATENT DOCUMENTS

| | | | |
|---|---|---|---|
| 1,904,751 | 4/1933 | Reerink et al. | 204/159 |
| 4,001,096 | 1/1977 | Salmond | 204/159 |

FOREIGN PATENT DOCUMENTS

| | | | |
|---|---|---|---|
| 55-7215 | 1/1980 | Japan | 204/159 |

Primary Examiner—Howard S. Williams

Attorney, Agent, or Firm—Fliesler, Dubb, Meyer & Lovejoy

[57] ABSTRACT

An improved method is set out for converting a reactant having a reactant core portion, 5,7-androstadiene-1α,3β-diol, into a product having a product core portion, 9,10-seco-5(10),6,8-androstatriene-1α,3β-diol. The core portions have a group, R, attached at the 17 position wherein R is any group which does not significantly effect the absorption characteristics of the reactant core portion in a range from about 280 nm to about 310 nm. The reaction is carried out by irradiating the reactant with radiation restricted substantially solely to be in the range from about 280 nm to about 310 nm. The improvement of the invention comprises maintaining the temperature of the reactant, during the irradiating, below about 0° C. and controlling the total doses of radiation to be such that (1) undesirable byproducts are not produced in an amount of more than about 15% and (2) at least about 60% of the product is produced based upon the quantity of the reactant consumed. The method gives yields of at least double that obtainable with prior art methods.

6 Claims, No Drawings

EFFICIENT PHOTOCHEMICAL FORMATION OF 1-α-HYDROXYPREVITAMIN D₃

This invention was made with Government Support under AM 00709 awarded by the Department of Health and Human Services. The Government has certain rights in this invention.

TECHNICAL FIELD

This invention relates to a method for converting a reactant having a reactant core portion, 5,7-androstadiene-1α,3β-diol, into a product having a product core portion, 9,10-seco-5(10),6,8-androstatriene-1α,3β-diol. In particular, 1α-hydroxyprovitamin D₃ is convertible into 1α-hydroxyprevitamin D₃.

BACKGROUND ART

The photochemical conversion of reactants having a reactant core portion of 5,7-androstadiene-1α,3β-diol, into a product having an altered product core portion, 9,10-seco-5(10),6,8-androstatriene-1α,3β-diol, is known. Furthermore, it is known that this reaction proceeds most efficiently when the irradiating light is restricted to being in the range from about 275 or 280 nm (nanometers) to about 310 nm. Such is discussed, for example, by Sato, et al, J. Nutr. Sci. Vitaminol. 26, 545–556, 1980; in Sato, et al Chem. Pharm. Bull. 26 (10) 2933–2940 (1978); and Barton, et al, J. Am. Chem. Soc. 95, 2748–2749 (1973). Unfortunately, relatively low yields, of the order of 15 to 40%, of 1α-hydroxyprevitamin D₃ are producible by the prior art methods. And, such methods have normally produced relatively great amounts of undesirable byproducts through decomposition of materials in the reaction mixture.

A method of producing 1α-hydroxyprevitamin D₃ in better yields and with less destruction of valuable starting 1α-hydroxyprovitamin D₃, and of producing related compounds, would be highly desirable.

The present invention is directed to overcoming one or more of the problems as set forth above.

DISCLOSURE OF INVENTION

The invention is concerned with a method for converting a reactant having a reactant core portion, 5,7-androstadiene-1α,3β-diol, into a product having an altered product core portion, 9,10-seco-5(10),6,8-androstatriene-1α,3β-diol. The reactant core portion and the product core portion both have a group, R, attached at the 17 position, wherein R is any group which does not significantly effect the absorption characteristics of the reactant core portion in the range from about 270 nm to about 330 nm. In the method of the invention the reactant is irradiated with radiation restricted substantially solely within the range from about 280 nm to about 310 nm. The improvement of the invention comprises maintaining the temperature of the reactant during the radiating below about 0° C. and controlling the total dose of radiation to be such that (1) undesirable byproducts are not produced in an amount of more than about 15% and (2) at least about 60% of the product is produced, based upon the quantity of the reactant consumed. Through proper control of the reaction temperature and the total dose of radiation much higher yields of 1α-hydroxyprevitamin D₃ can be obtained from 1α-hydroxyprovitamin D₃ than can be attained by prior art synthetic methods. Furthermore, decomposition of materials in the reaction mixture is kept relatively low, thus providing an efficient and inexpensive process.

BEST MODE FOR CARRYING OUT THE INVENTION

In accordance with the present invention, it has been discovered that reactants having a core portion, 5,7-androstadiene-1α,3β-diol, can be converted into a product having an altered core portion, namely, 9,10-seco-5(10),6,8-androstatriene-1α,3β-diol in very improved yields through controlling the radiation dose and the temperature of the reactant during the irradiation to be such that undesirable byproducts are not produced in an amount of more than about 15%, more preferably about 10%, and most preferably about 5% and the temperature is generally controlled to be below about 0° C., preferably below about −20° C., and still more preferably below about −40° C. The reaction conditions can be controlled to produce at least about 60%, and more preferably at least about 75%, of the product based upon the quantity of the reactant consumed. Indeed, it has been found possible to to obtain over 80% of the product based upon the quantity of the reactant consumed, utilizing relatively ideal reaction conditions.

As was previously known, for efficient photoreaction it is necessary that the radiation impinging upon the reactant be within a range from about 280 nm to about 310 nm. One of the discoveries of the present invention is that if the wavelength of the light is very strictly controlled, as by using a 300 nm laser, then over 80% of the desired product can be produced when the reaction temperature is about −20° C. When a more wide ranging light source is used, for example a light source which radiates substantially solely in the range of about 280 nm to about 310 nm, but which has significant radiation over this entire range and even produces some radiation outside of this range, then it is necessary to go to a lower temperature in order to obtain equivalent yields. For example, with one such lamp, namely a Rayonet (Trademark of the Southern New England Ultra Violet Company) Model RU-3000Å is utilized, about an 83% yield of the desired product is obtained at a temperature of approximately −55° C. And, this is obtained with only about 4% of undesirable byproducts resulting. Structurally, the reactant would have the structural formula:

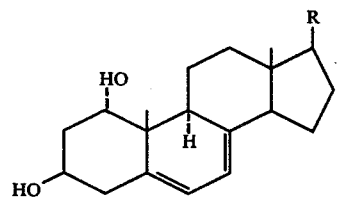

The product would normally have the structural formula:

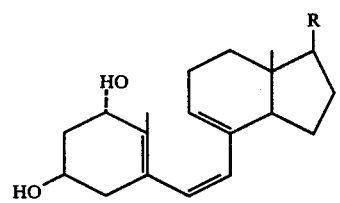

In the above formulas the group, R, attached at the 17 position to the molecule, can be any group which does not significantly effect the absorption characteristics of the reactant core portion. When the reactant is 1α-hydroxyprovitamin D$_3$ its structure is:

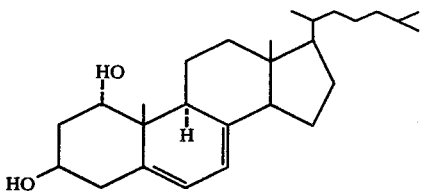

When the product is 1α-hydroxyprevitamin D$_3$ its structure is:

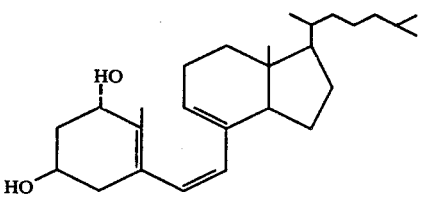

The invention will be better understood by references to the following illustrative examples which provide actual experimental data.

EXAMPLE 1

Use Of Laser Source

A 0.004 M solution of 1α-hydroxy-7-dehydrocholesterol in dry ether was irradiated with 300 nm light from a CMX-4 laser (6 kv/pulse, 15 pps, 5 n watts, rhodamine 6-G in methanol) and the reaction was monitored by HPLC using progesterone as a standard.

0° C. Results: When the reaction was carried out at 0° C. the formation of 1α-hydroxyprevitamin D$_3$ leveled off at a maximum yield of about 22%. The amount of the starting material, the 1α-hydroxyprovitamin D$_3$, continued to decrease, 60% having been consumed at this leveling off stage. The formation of undesirable byproducts, i.e., decomposition of materials, continued at a steady rate and at the leveling off point for 1α-hydroxyprevitamin D$_3$ formation, the decomposed material amounted to 45% of the total reaction mixture.

−21° C. Results: The same laser irradation was conducted but at a reduced temperature of −21° C. A different reaction profile resulted. The formation of 1α-hydroxyprevitamin D$_3$ leveled off at 54%. The combined 1α-hydroxyprovitamin D$_3$ and 1α-hydroxylumisterol (the two of which could not be separated form one another under the HPLC conditions used) amounted to 22%. 1α-hydroxytachysterol was found. The undesirable byproducts amounted to only 14%. From a study of the reaction profile it became evident that the maximum yield of the 1α-hydroxyprevitamin D$_3$, based upon the recovered mixture of potential 1α-hydroxyprevitamin D$_3$ precursors, was 50% at 40% recovery of the mixture of 1α-hydroxyprovitamin and 1α-hydroxylumisterol derivative. Under those conditions only 2% of undesirable byproducts was present. Thus, the yield of 1α-hydroxyprevitamin D$_3$ was 83% at that time based upon the quantity of the 1α-hydroxyprovitamin D$_3$ consumed as determined by measuring the recovered 1α-hydroxyprevitamin D$_3$ precusor.

EXAMPLE II

Use of Commercial 300 nm Light Source

An irradiation was carried out as previously described with the exception that a commercial 300 nm Rayonet light source was utilized in place of the laser. The reaction was carried out at 0° C., −25° C., and −55° C. As the temperature was changed in this manner the maximum amount of 1α-hydroxyprevitamin D$_3$, increased from 25% to 33%. A study of the reaction profile showed that at −55° C. the maximum yield was reached after conversion of only 40% of the 1α-hydroxyprevitamin D$_3$. At the higher temperature the yield is not maximized until after 70% conversion. These results reflect a more rapid build up of undesirable byproducts at the higher temperatures. At −55° C. and 40% conversion approximately 6% of the 1α-hydroxytachysterol derivative had been formed and only 4% of undesirable byproducts were present. Thus, at −55° C. and 40% conversion the yield of 1α-hydroxyprevitamin D$_3$ was 83% based upon the amount of recovered 1α-hydroxyprevitamin D$_3$ precursor.

Industrial Applicability

The invention operates to provide much improved yields of such compounds as 1α-hydroxyprevitamin D$_3$ from such compounds as 1α-hydroxyprovitamin D$_3$.

We claim:

1. In a method for converting a reactant core portion, 5,7-androstadiene-1α,3β-diol, into a product having a product core portion, 9,10-seco-5(10),6,8-androstatriene-1α,3β-diol, said reactant core portion and said product core portion having a group, R, attached at the 17 position, wherein, R, is any group which does not significantly effect the absorption characteristics of said reactant core portion in the range from about 280 nm to about 310 nm, comprising irradiating the reactant with radiation restricted substantially solely to be in the range from about 280 nm to about 310 nm, an improvement which comprises:

maintaining the temperature of the reactant, during the irradiating, below about −20° C.; and
   controlling the total dose of radiation to be such that (1) undesirable byproducts are not produced in an amount of more than about 15%, (2) at least about 60% of said product is produced based upon the quantity of the reactant consumed and (3) at least about 40% of the reactant is consumed.

2. A method as set forth in claim 1, wherein said irradiating is by 300 nm laser.

3. A method as set forth in claim 1, wherein said irradiating is by a lamp structure radiating over substantially all of the range from about 280 nm to about 310 nm.

4. A method as set forth in claim 3, wherein said product is recovered in a yield of at least about 75% based upon the quantity of the reactant consumed.

5. A method as set forth in claim 4, wherein the reactant comprises 1α-hydroxyprovitamin D$_3$ and the product comprises 1α-hydroxyprevitamin D$_3$.

6. A method as in set forth in claim 1, wherein the temperature is below about −40° C.

* * * * *

UNITED STATES PATENT AND TRADEMARK OFFICE
CERTIFICATE OF CORRECTION

PATENT NO. : 4,490,226
DATED : December 25, 1984
INVENTOR(S) : William G. Dauben et al It is certified that error appears in the above-identified patent and that said Letters Patent is hereby corrected as shown below:

Column 3, line 56, "1α-hydroxytachysterol" should be "1α-hydroxytachysterol$_3$".

Column 4, lines 15, 16, "1α-hydroxyprevitamin $D_3$" should be "1α-hydroxyprovitamin $D_3$".

Signed and Sealed this

Twenty-first Day of May 1985

[SEAL]

Attest:

DONALD J. QUIGG

*Attesting Officer*     *Acting Commissioner of Patents and Trademarks*